: US009822087B2

United States Patent
Arrowood et al.

(10) Patent No.: US 9,822,087 B2
(45) Date of Patent: Nov. 21, 2017

(54) ASSEMBLY FOR PRODUCING ALKYLENE OXIDES AND GLYCOL ETHERS

(71) Applicant: DOW GLOBAL TECHNOLOGIES LLC, Midland, MI (US)

(72) Inventors: Tina L. Arrowood, Minneapolis, MN (US); Derrick W. Flick, Freeport, TX (US); John F. Ackford, Midland, MI (US)

(73) Assignee: Dow Global Technologies LLC

( * ) Notice: Subject to any disclaimer, the term of this patent is extended or adjusted under 35 U.S.C. 154(b) by 0 days.

(21) Appl. No.: 15/043,368

(22) Filed: Feb. 12, 2016

(65) Prior Publication Data

US 2016/0159761 A1 Jun. 9, 2016

Related U.S. Application Data

(62) Division of application No. 14/806,498, filed on Jul. 22, 2015, now Pat. No. 9,273,019, which is a division
(Continued)

(51) Int. Cl.
*B01J 19/00* (2006.01)
*B01J 19/24* (2006.01)
(Continued)

(52) U.S. Cl.
CPC .......... *C07D 301/32* (2013.01); *B01J 19/245* (2013.01); *C07D 301/12* (2013.01); *C07D 301/36* (2013.01); *B01J 2219/24* (2013.01)

(58) Field of Classification Search
CPC . B01J 19/00; B01J 19/24; B01J 19/245; B01J 2219/24; C07D 301/00–301/03;
(Continued)

(56) References Cited

U.S. PATENT DOCUMENTS 3,972,948 A * 8/1976 Laemmle ................ C07C 41/03
568/618
5,274,138 A * 12/1993 Keating ................ C07C 29/132
549/529
(Continued)

FOREIGN PATENT DOCUMENTS

CN 1295068 A 5/2001
CN 1440397 A 9/2003
(Continued)

OTHER PUBLICATIONS

Haisheng, et al., "Research on the Reaction Condition of the Synthesis of Propylene Glycol Monomethyl Ether by C3H6 and H2O2 with Catalysis of TS-1 Zeolite", Shiyou Xuebao, Shiyou Jiagong, vol. 17, Supplement, Zhongguo Shihua Chubanshe, 2001, 59-65.
(Continued)

*Primary Examiner* — Natasha Young

(57) ABSTRACT

There is provided a manufacturing assembly for the production of an alkylene oxide and a stream of glycol ethers. The manufacturing assembly produces the alkylene oxide and stream of glycol without the use of equipment for separating substantially all of the alkyl alcohol from the alkylene oxide product stream. Thus, the use of additional pieces of equipment can be avoided, or the equipment required to effectuate any required further separation and/or purification may be smaller and/or cheaper to purchase and/or operate.

6 Claims, 1 Drawing Sheet

Related U.S. Application Data of application No. 13/808,594, filed as application No. PCT/US2011/042107 on Jun. 28, 2011, now Pat. No. 9,169,226.

(60) Provisional application No. 61/364,231, filed on Jul. 14, 2010.

(51) Int. Cl.
| | | |
|---|---|---|
| *C07D 301/00* | (2006.01) | |
| *C07D 301/02* | (2006.01) | |
| *C07D 301/03* | (2006.01) | |
| *C07D 301/32* | (2006.01) | |
| *C07D 301/36* | (2006.01) | |
| *C07D 301/12* | (2006.01) | |

(58) Field of Classification Search
CPC ... C07D 301/12; C07D 301/32; C07D 301/36
See application file for complete search history.

(56) References Cited

U.S. PATENT DOCUMENTS

| | | |
|---|---|---|
| 5,849,938 A | 12/1998 | Rueter et al. |
| 6,448,414 B1 | 9/2002 | Jacobsen |
| 6,693,206 B2 | 2/2004 | Liu et al. |
| 6,723,861 B2 | 4/2004 | Balthasart |
| 6,800,766 B2 | 10/2004 | Jacobsen et al. |
| 6,846,961 B2 | 1/2005 | Teles |
| 6,881,853 B2 | 4/2005 | Teles et al. |
| 7,084,310 B2 | 8/2006 | Bassler et al. |
| 7,105,687 B1 | 9/2006 | Chang |
| 7,220,870 B2 | 5/2007 | Jacobsen et al. |
| 7,323,579 B2 | 1/2008 | Goebbel et al. |
| 7,378,536 B2 | 5/2008 | Goebbel et al. |
| 7,645,892 B2 * | 1/2010 | Jubin, Jr. ............... B01J 8/1836 261/114.1 |
| 2003/0166975 A1 | 9/2003 | Teles |
| 2006/0113180 A1 * | 6/2006 | Patrascu ............... B01D 3/38 203/76 |
| 2008/0289948 A1 | 11/2008 | Diefenbacher |

FOREIGN PATENT DOCUMENTS

| | | |
|---|---|---|
| WO | 9911639 | 3/1999 |
| WO | 2004083196 | 9/2004 |
| WO | 2010099300 | 9/2010 |
| WO | 2010099307 | 9/2010 |
| WO | 2010099309 | 9/2010 |

OTHER PUBLICATIONS

Martinez, et al., "Highly Enantioselective Ring Opening of Epoxides Catalyzed by (salen)Cr(III) Complexes", J. Am. Chem. Soc., vol. 117, 1995, 5897-5898.

Ready, et al., "Asymmetric Catalytic Synthesis of alpha-Aryloxy Alcohols: Kinetic Resolution of Terminal Epoxides via Highly Enantioselective Ring-Opening with Phenols", J. Am. Chem., vol. 121, 1999, 6086-6087.

Toknaga, et al., "Asymmetric Catalysis with Water: Efficient Kinetic Resolution of Terminal Epoxides by Means of Catalytic Hydrolysis", Science, vol. 277, Aug. 15, 1997, 936-938.

Yanglin, "One-Step Synthesis of Propylene Glycol Monomethyl Ether from Propylene", Wuhan Keji Daxue Xuebao, vol. 32(2), 2009, 213-216.

Zheng, et al., "Ring-Expanding Olefin Metathesis: A Route to Highly Active Unsymmetrical Macrocyclic Oligomeric Co-Salen Catalysts for the Hydrolytic Kinetic Resolution of Epoxides", J. Am. Chem. Soc., 2007, 1105-1112.

PCT/US2011/042107, International Search Report and Written Opinion dated Feb. 3, 2012.

* cited by examiner

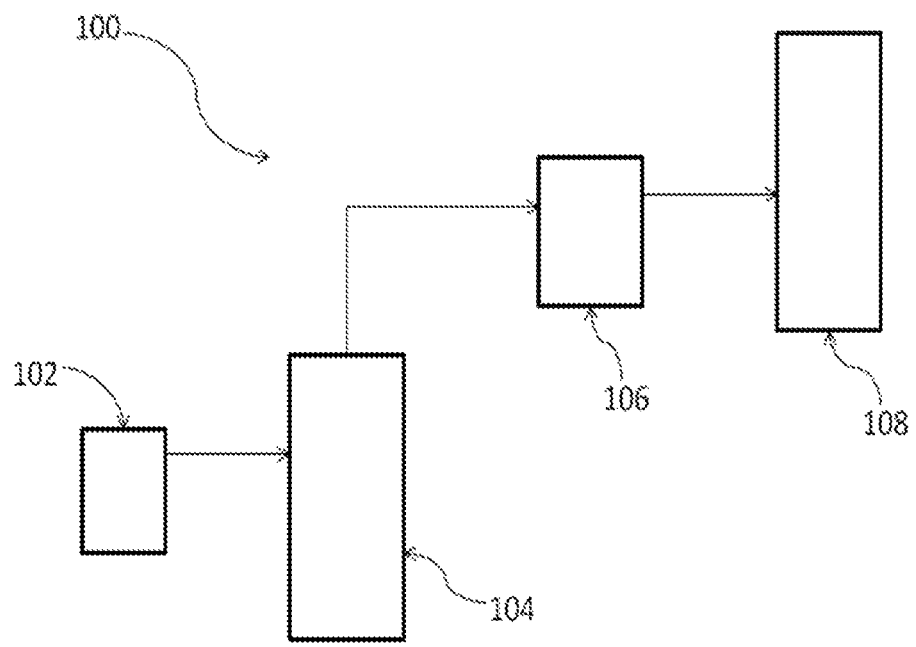

ASSEMBLY FOR PRODUCING ALKYLENE OXIDES AND GLYCOL ETHERS

CROSS-REFERENCE TO RELATED APPLICATIONS

This is a divisional application of U.S. patent application Ser. No. 14/806,498, now issued as U.S. Pat. No. 9,273,019, filed Jul. 22, 2015, which, in turn is a divisional application of U.S. patent application Ser. No. 13/808,594, filed Jan. 6, 2013, now issued as U.S. Pat. No. 9,169,226, which, in turn, is a 371 of International Application No. PCT/US2011/42107, now published as WO 2012/009155, filed Jun. 28, 2011, which, in turn, claims the benefit of U.S. provisional patent application Ser. No. 61/364,231, filed Jul. 14, 2010. The contents of the aforementioned applications are incorporated herein by reference in their entirety.

FIELD

The present invention relates to manufacturing assemblies for the production of an alkylene oxide and one or more glycol ethers. A process for manipulating the amount of an alkyl alcohol in a product stream comprising an alkylene oxide and a process for producing an alkylene oxide and one or more glycol ethers incorporating the process is also provided.

BACKGROUND

Alkylene oxides may be prepared by reaction of an alkylene and hydrogen peroxide, hydroperoxide, or oxygen and hydrogen. Generally, these reactions are carried out in a liquid solvent, e.g., an alkyl alcohol and water, and in the presence of a solid, metal containing catalyst. However, the use of one or more alkyl alcohols as a solvent can be problematic in that the separation of the same from the desired alkylene oxide requires energy intensive distillation operations comprising a large number of trays, and operated at high reflux rates. In order to reduce the economic burden imposed by the use of the alkyl alcohol, a majority, if not all, of the alkyl alcohol may typically be recycled once separated from the alkylene oxide.

In order to further reduce this burden, alternative separation techniques have been proposed, many involving the use of extractive distillation. However, the proposed solutions often introduce additional problems. For example, the addition of an extraction solvent increases the size requirement of the distillation column used to remove the alkyl alcohol due to the added volume of the extraction solvent.

Desirably, methods for the production of alkylene oxide would be developed that provide for the separation of an alkyl alcohol from an alkylene oxide with reduced difficulty and/or economic burden as compared to conventional or extractive distillation methods.

BRIEF DESCRIPTION

The present invention provides such a process. More specifically, the present invention provides a process for manipulating the amount of an alkyl alcohol in a mixture, e.g., such as an alkylene oxide product stream. More particularly, and in contrast to conventional processes wherein substantially all of the alkyl alcohol must be separated and desirably recycled, in the present process, a greater amount of alkyl alcohol may be allowed to remain in a partially refined alkylene oxide product stream. The residual alkyl alcohol is subsequently substantially entirely reacted to form one or more downstream products, e.g., one or more glycol ethers, which are more easily separated from the alkylene oxide product stream. Indeed, the amount of alkyl alcohol in the partially refined alkylene oxide product stream can be selected based upon the output of the desired one or more glycol ethers, if desired. Advantageously, the volume of feed to the alkylene oxide refining process is not increased, as may be the case when extractive distillation techniques are utilized to achieve a similar purpose. Furthermore, because the use of extractive distillation can be avoided, the capital and energy costs associated with the same are also eliminated.

In one aspect then, the present invention provides a process for manipulating the amount of an alkyl alcohol in a mixture, wherein the mixture comprises from about 5 to about 15 weight percent alkylene oxide, about 50 to about 85 weight percent alkyl alcohol and about 10 to about 25 weight percent water. The process comprises introducing the mixture into a distillation column to produce a refined stream comprising from about 50 to about 99 weight percent alkylene oxide, about 0.5 to about 50 weight percent alkyl alcohol and about 0 to about 5 weight percent water. In some embodiments, the refined stream may comprise from about 65 to about 99 weight percent alkylene oxide, about 0.5 to about 35 weight percent alkyl alcohol and about 0 to about 5 weight percent water. The refined stream is then reacted with a catalyst comprising a metal-ligand complex, an acid, a base, a metal alkoxide, or a combination of any number of these to reduce the alkyl alcohol content in a resulting reacted stream to less than 1 wt %.

Such a mixture may typically be found in, e.g., an alkylene oxide product stream, and so, the process may advantageously be incorporated into processes for the production of an alkylene oxide and one or more glycol ethers. In a further aspect, the present invention thus provides a process for the preparation of an alkylene oxide and one or more glycol ethers. The process comprises reacting an alkylene with hydrogen peroxide, a hydroperoxide, or hydrogen and oxygen under conditions sufficient to produce a product stream comprising the desired alkylene oxide. The process comprises introducing the mixture into a distillation column to produce a refined stream comprising from about 50 to about 99 weight percent alkylene oxide, about 0.5 to about 50 weight percent alkyl alcohol and about 0 to about 5 weight percent water. In some embodiments, the refined stream may comprise from about 65 to about 99 weight percent alkylene oxide, about 0.5 to about 35 weight percent alkyl alcohol and about 0 to about 3 weight percent water. The refined product stream is then reacted with a catalyst comprising a metal-ligand complex, an acid, a base, or a combination of any number of these to produce a reacted stream comprising less than 1 wt % alkyl alcohol, from about 0.5 to about 98 weight percent alkylene oxide and from about 2 to about 99 weight percent glycol ethers. The refined, reacted product stream is then introduced into a second distillation column to provide a substantially pure stream of alkylene oxide and a stream of glycol ethers.

Because the present processes allow for the presence of a greater amount of alkyl alcohol in the partially refined alkylene oxide stream than conventional processes, and indeed for the manipulation of the same based upon the desired production of glycol ethers, the use of separation techniques capable of separating substantially all of the alkyl alcohol from the alkylene oxide product stream are not required. And so, the use of additional pieces of equipment can be avoided, or the equipment required to effectuate any required further separation and/or purification may be smaller and/or cheaper to purchase and/or operate. Furthermore, the operation of a second reaction step in the process both produces a substantially pure stream of alkylene oxide and a substantially pure stream of useful glycol ethers. And so, in another aspect, a hybrid manufacturing assembly for the production of an alkylene oxide and a stream of glycol ethers is provided.

The hybrid manufacturing assembly comprises a reactor appropriate for housing a reaction to produce an alkylene oxide product stream comprising from about 5 to about 15 weight percent alkylene oxide, about 50 to about 85 weight percent alcohol and about 10 to about 25 weight percent water. The assembly further comprises a distillation column operatively disposed relative to the reactor to receive the alkylene oxide product stream thereof, comprising fewer than 80 theoretical stages and appropriate for producing a refined stream comprising from about 50 to about 99 weight percent alkylene oxide, about 0.5 to about 50 weight percent alkyl alcohol and about 0 to about 5 weight percent water, or from about 65 to about 99 weight percent alkylene oxide, about 0.5 to about 35 weight percent alkyl alcohol and about 0 to about 5 weight percent water. The assembly also comprises a vessel operatively disposed relative to the distillation column to receive the refined stream therefrom and housing a catalyst capable of reacting with the refined stream to produce a reacted stream comprising less than 1 wt % alkyl alcohol, from about 0.5 to about 98 weight percent alkylene oxide and from about 2 to about 99 weight percent glycol ethers. Finally, the hybrid assembly comprises a second distillation column operatively disposed relative to the vessel to receive the reacted stream to produce a substantially pure stream of alkylene oxide and a stream of glycol ethers.

BRIEF DESCRIPTION OF THE DRAWINGS

These and other features, aspects, and advantages of the present invention will become better understood when the following detailed description is read with reference to the accompanying drawings, wherein:

FIG. 1 is a schematic illustration of a manufacturing assembly according to one embodiment.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). Furthermore, weight percents are used to define many of the ranges herein. Although these ranges are expected to include many of the embodiments of the invention, they were calculated based upon one embodiment, i.e., that embodiment wherein the alkyl alcohol is methanol and the alkylene oxide comprises propylene oxide. Those of ordinary skill in the art will recognize that these ranges may vary if different members of these genus' are utilized.

The modifier "about" used in connection with a quantity is inclusive of the stated value and has the meaning dictated by the context (e.g., includes the degree of error associated with measurement of the particular quantity). Unless otherwise defined, all percents are provided as weight percents. The suffix "(s)" as used herein is intended to include both the singular and the plural of the term that it modifies, thereby including one or more of that term (e.g., "the catalyst(s)" may include one or more catalysts). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

The present invention provides a process for manipulating the amount of an alkyl alcohol in a mixture, e.g., such as a partially refined alkylene oxide product stream. More particularly, and in contrast to conventional processes wherein substantially all of the alkyl alcohol must be separated and desirably recycled, in the present process, a greater amount of alkyl alcohol may be allowed to remain in a partially refined alkylene oxide product stream. The residual alkyl alcohol is subsequently substantially entirely reacted to form one or more downstream products, e.g., one or more glycol ethers, which is/are more easily separated from the alkylene oxide product stream. In such embodiments, overall process yield/specificity may advantageously be increased.

The mixture subjected to the present process may be any mixture wherein the alkyl alcohol content thereof is desirably manipulated, e.g., reduced, without application of conventional and/or extractive distillation processes, which can add extra cost to the process in that the extraction solvent typically must later be removed and optionally recovered and recycled. Exemplary mixtures that find particular benefit in application of the present process include those that comprise not only a relatively high amount, e.g., greater than about 50 wt %, or greater than about 60 wt % or greater than 70 wt % or even greater than about 85 wt %, of an alkyl alcohol, but also amounts of alkylene oxide and water.

More particularly, the mixture to which the process may advantageously be applied may comprise from about 5 to about 15 weight percent alkylene oxide, about 50 to about 85 weight percent alkyl alcohol and about 10 to about 25 weight percent water, based upon the total weight of the mixture. Or, the mixture may comprise from about 6 to about 12 weight percent alkylene oxide, about 60 to about 80 weight percent alkyl alcohol and about 10 to about 20 weight percent water. In some embodiments, the process described herein may even be applied to mixtures comprising from about 8 to about 10.5 weight percent alkylene oxide, about 65 to about 75 weight percent alkyl alcohol and about 10 to about 15 weight percent water.

The mixture may comprise any alkyl alcohol desirably separated from such a mixture. Desirably, the alkyl alcohol to be separated will be one typically present in mixtures also comprising amounts of one or more alkylene oxides. Alkyl alcohols typically present in mixtures also comprising one or more alkylene oxides generally include methanol, ethanol, propanol, butanol, pentanol, hexanol, 2-ethylhexyl alcohol, or combinations of any of these. In some processes for the production of alkylene oxides, methanol may typically be used as a solvent and thus, in some embodiments, the alkyl alcohol may advantageously comprise methanol.

The mixture also comprises at least one alkylene oxide. Any alkylene oxide may be present, and typical alkylene oxides are exemplified by, but are not limited to, ethylene oxide, propylene oxide, butylene oxide, pentylene oxide, hexylene oxide and combinations thereof. In some embodiments, the alkylene oxide(s) may comprise ethylene oxide, propylene oxide, butylene oxide or combinations of these. Because of its commercial importance and widespread use in the production of glycol ethers, in some embodiments, the alkylene oxide may desirably comprise propylene oxide.

Whatever the desired mixture, it is initially introduced into a distillation column to provide a more concentrated stream of alkylene oxide. The refined stream will desirably comprise from about 50 to about 99 weight percent alkylene oxide, about 0.5 to about 50 weight percent alkyl alcohol and about 0 to about 5 weight percent water. In some embodiments, e.g., wherein the alkyl alcohol comprises methanol and the alkylene oxide comprise propylene oxide, the refined stream may comprise from about 65 to about 99 weight percent alkylene oxide, about 0.5 to about 35 weight percent alkyl alcohol and about 0 to about 5 weight percent water. Or, in such embodiments, the refined stream may comprise from about 70 to about 95 weight percent alkylene oxide, from about 1 weight percent to about 30 wt % alkyl alcohol and from about 0.1 weight percent to about 4.9 wt % water. Or, the refined stream may comprise from about 70 to about 90 wt % alkylene oxide, from about 10 weight percent to about 30 wt % alkyl alcohol and from about 1 weight percent to about 4 wt % water.

Generally speaking, the distillation operation may comprise fewer than 80 theoretical stages, and may comprise, e.g., from about 15 to about 70 theoretical stages, or from about 30 to about 60 theoretical stages. Conventional distillation process utilized to separate such mixtures may typically require the utilization of 80 or more stages, and so, by virtue of the application of the principles described herein, the theoretical stages, and energy input, required to conduct the separation can be reduced. One or more columns may be utilized that provide the desired total number of stages/plates, and in some embodiments, one column may be sufficient, while also provide space, energy and capital savings.

The distillation column utilized to provide the refined stream will further desirably have a bottoms temperature of from about 40° C. to about 70° C., or from about 46° C. to about 64° C., or from about 52° C. to about 62° C. The distillation may be carried out at pressures of from about 300 mbar to about 1000 mbar, or from about 400 mbar to about 800 mbar, or from about 500 mbar to about 700 mbar, as measured at the top of the column. Suitable combinations of temperature and pressure for the distillation include from about 40° C. to about 70° C. and from about 300 mbar to about 1000 mbar, or from about 46° C. to about 64° C. and from about 400 mbar to about 800 mbar, or from about 52° C. to about 62° C. and from about 500 mbar to about 700 mbar.

The refined stream is then reacted with a catalyst to reduce the alkyl alcohol content in a resulting reacted stream to less than 1 wt %. More particularly, the reacted stream may comprise less than 1 wt % alkyl alcohol, from about 0 wt % to about 98 wt % alkylene oxide, and from about 2 wt % to about 99 wt % glycol ethers, or less than about 0.8 wt % alkyl alcohol and from about 10 wt % to about 90 wt % alkylene oxide, and from about 10 wt % to about 90 wt % glycol ethers, or less than about 0.7 wt % alkyl alcohol and from about 50 wt % to about 85 wt % alkylene oxide, and from about 15 wt % to about 50 wt % glycol ethers.

The particular glycol ethers obtainable will depend upon the particular composition of the starting mixture, i.e., the particular alkyl alcohol and alkylene oxide in the mixture, as well as the particular catalyst chosen. For mixtures comprising, e.g., methanol and propylene oxide, the stream of glycol ethers may typically comprise dipropylene glycol monomethyl ether (DPM) and monopropylene glycol methyl ethers (PM). In some particularly advantageous embodiments of the present method, the catalyst utilized to react with the refined stream can provide a greater percentage of the PM homologue in the glycol ethers stream than DPM, e.g., the reacted stream may comprise greater than 90%, or greater than 95% or even greater than 98% of PM, and less than 10%, or even less than 5% or even less than 2% DPM.

Further advantageous is the fact that the PM homologue typically further comprises greater than 95%, or greater than 97%, or even greater than 99% or even greater than 99.7% 1-methoxy-2-propanol (PM2) and less than 5%, or less than 3%, or less than 1%, or even less than 0.3% 2-methoxy-1-propanol (PM1). PM2 is not only easily separated from propylene oxide with minimal theoretical stages, but also, is easily provided into salable product specifications via the same. Separating PM1 from PM2 to the levels required to provide a salable PM2 product can be difficult and costly, since distillation is used to separate these similar boiling materials (PM2 boiling point at 1 atm (bp)=118-119° C.; PM1 bp=130° C.).

And so, the catalyst utilized is desirably one exhibiting a high activity and/or high selectivity in the alkanolysis of alkylene oxide. Such catalysts include, but are not limited to, acidic, basic, and neutral catalytic species as well as metal-ligand complexes. The catalyst can be heterogenous or homogenous. Suitable catalysts are disclosed, for example in, K. Tanabe, M. Misono, Y. Ono, H. Hattori "Studied in Surface Science and Catalysis. New Solid Acids and Bases: Their Catalytic Properties" 1989, Vol. 51. pp. 1-3. H. Hattori "Heterogeneous Basic Catalysts" *Chem. Rev.* 1995, 95, 537-558, U.S. Pat. No. 4,360,698 to Sedon, and U.S. Pat. No. 2,807,651 to Britton, each of these being incorporated herein by reference in its entirety for any and all purposes.

Examples of suitable acidic catalytic species include, but are not limited to, metal triflates, metal tosylates, trisperfluoronated aryl borons, p-toluenesulfonic acid, phosphoric acid, sulfuric acid, boric acid, fluorine containing acids, chloric acids, acidic ion exchange resin, acidic alumina, zeolites, acid modified silicas, aluminas, or silica-aluminas, metal oxides and sulfides, mounted acids on silica, quartz sand, alumina or diatomaceous earth, mixed oxides, metal salts, heat treated charcoal, or combinations thereof. In some embodiments wherein the catalyst is desirably acidic, aluminum triflate may desirably be used.

Examples of suitable basic catalytic species include, but are not limited to, metal hydroxides, metal carbonates, metal oxides, substituted or unsubstituted imidazoles, substituted or unsubstituted amines, substituted or unsubstituted pyridines, metal alkoxides, basic ion-exchange resins, basic alumina, alkali ion-exchanged zeolites, hydrotalcites, chrysotile, sepiolite, KF supported on alumina, lanthanide imide, nitride on zeolite, or combinations thereof. In some embodiments, substituted or unsubstituted imidazole(s) and/or potassium hydroxide and/or sodium hydroxide, may be used if use of a basic catalyst is desired.

Furthermore, suitable metal-ligand complexes include, but are not limited to, monomers according to Formula I:

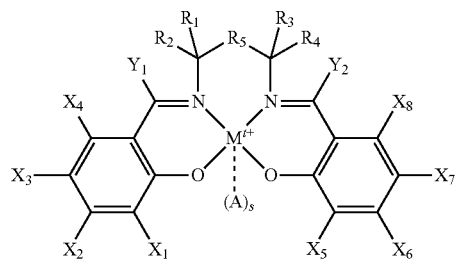

wherein $R_1$, $R_2$, $R_3$, $R_4$, $Y_1$, $Y_2$, $X_1$, $X_2$, $X_3$, $X_4$, $X_5$, $X_6$, $X_7$, and $X_8$ comprise, independently of one another, substituents selected from the group consisting of hydrogen, halogen, alkyl, alkenyl, alkynyl, hydrocarbyl, hydroxyl, alkoxyl, amino, nitro, amide, phosphoryl, phosphonate, phosphine, carbonyl, carboxyl, silyl, ether, thioether, sulfonyl, selenoether, ketone, aldehyde, and ester;

or wherein two or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ together form a ring selected from the group consisting of a carbocyclic ring and a heterocyclic ring, said ring having from 4 to 10 atoms in the ring;

wherein $R_5$ group is selected from the group comprising a carbon-carbon bond, a methylene group, an ethylene group, an amine, an oxygen atom, and a sulfur atom;

wherein $M^{t+}$ is a Group 2-15 metal capable of complexing with a ligand to affect catalysis, wherein t is an integer between 2 and 4;

wherein group A is selected from the group consisting of neutral group, bound anionic group, unbound anionic group, and combinations thereof, wherein s is the number of A groups associated with the metal and is an integer between 0 and 2.

In some embodiments of the invention, M is cobalt and A comprises carboxylate, sulfonate, halide, alkoxide, hexafluorophosphate, tetrafluoroborate, hexafluoroantimonate or bis(trialkylsilyl)amide. In one particular embodiment of the invention, A is 3-nitrobenzenesulfonate and s=1.

In some embodiments, one or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ may be capable of providing a complementary interaction with a second monomer, either according to formula I or otherwise, to form a component selected from the group consisting of oligomer, polymer, and copolymer. For example, in some embodiments, the metal-ligand complex may comprise an oligomer comprising from about 1 to about 20 repeating units of the monomer.

In some embodiments, the metal-ligand complex is bound to a support. Examples of supports that can be used include, but are not limited to, an organic polymer, an ion-exchange resin, an inorganic support, a metal organic framework, and carbon. The catalyst can be incorporated into or onto the support by any suitable method known to those skilled in the art including, but not limited to, covalent bonding, ionic bonding, hydrogen bonding, metal complexing, encapsulating, and intercalating.

The following documents provide examples of supporting techniques and their entire contents are hereby incorporated herein by reference for any and all purposes: Baleizo, et. al. *Chemical Reviews* 2006, 106(9), 3987-4043; Orejón, et al., *Industrial and Engineering Chemical Research* 2008, 47(21), 8032-8036; Yang, et al., *Journal of Catalysis* 2007, 248, 204-212; Kim, et. al., *Catalysis Today* 2000, 63, 537-547.

Any of the above catalysts can be incorporated into polymeric structures by utilizing any of several different methods known to those of ordinary skill in the art. The following documents provide examples of such techniques: Hu, et al., *Journal of Applied Polymer Science* 2006, 101, 2431-2436 Song, et al., *Tetrahedron Letters* 2003, 44, 7081-7085, Kwon, et al., *Catalysis Today* 2003, 87, 145-151, Gill, et al., *Chemistry—A European Journal* 2008, 14, 7306-7313, Zheng, et al., *Chemistry—A European Journal* 2006, 12, 576-583, Zheng, et al., *Advanced Synthesis and Catalysis* 2008, 350, 255-261. Each of these is incorporated by reference herein in their entirety for any and all purposes.

If desired, a cocatalyst may be used in the process. Generally, suitable cocatalysts comprise Lewis acid(s). Examples of Lewis acids that can be used, if desired, include, but are not limited to metal triflates, metal tosylates, tris-perfluoronated aryl boron, metal halides, and combinations thereof. One non-limiting example of a metal triflate that can be used is aluminum triflate. When a cocatalyst is used, the mole ratio of the catalyst (and in those embodiments wherein the catalyst is the monomer above, the mole ratio of the monomeric unit) to the co-catalyst is generally in the range of from about 1:1 to about 20:1.

The refined stream is reacted with the desired catalyst under reaction conditions appropriate given the composition of the refined stream and the chosen catalyst. Generally speaking, suitable reaction conditions may comprise a temperature in the range of from about −10° C. to about 200° C., or from about 0° C. to about 150° C., or from about 10° C. to about 100° C., or from about 15° C. to about 60° C. The reaction may take place in any suitable vessel or zone, including a fixed bed, a fluidized bed, a continuous stirred tank reactor (CSTR), batch, semi-batch, continuous types or combinations thereof. The desired vessel can be operated isothermally, adiabatically, or a combination thereof.

In some embodiments, the reacted stream may be provided to a second distillation column to provide a substantially pure stream of alkylene oxide and a stream of glycol ethers. In some embodiments, the alkylene oxide may be propylene oxide, and the stream of glycol ethers may comprise substantially PM2.

Those of ordinary skill in the art will be capable of determining the distillation conditions capable of producing a stream of substantially pure alkylene oxide and a stream of glycol ethers from the reacted stream, described above, the parameters of distillation being well known in the art. One or more columns may be utilized that provide the desired total number of stages/plates, and thus, the desired separation, and in some embodiments, one column may be sufficient, while also providing space, energy and capital savings.

By utilizing the present process, the volume of feed into a process for the production of alkylene oxide is not increased, in contrast to methods that rely on, e.g., extractive distillation to achieve a similar purpose. Furthermore, since no volume is added in the present process, it need not later be separated from the desired product stream as is required with conventional processes that may employ, e.g., extractive distillation. Because the use of extractive distillation can be avoided, the capital and energy costs associated with the same are also eliminated. Additionally, the present process provides a flexible method for converting a part of the propylene oxide to a higher value glycol ether product. And, for mixtures comprising, e.g., methanol and propylene oxide, the stream of glycol ethers may typically comprise greater than 90%, or greater than 95% or even greater than 98% of monopropylene glycol methyl ethers (PM), and less than 10%, or even less than 5% or even less than 2% dipropylene glycol monomethyl ether (DPM). Advantageously, the PM homologue typically further comprises greater than 95%, or greater than 97%, or even greater than 99% or even greater than 99.7% 1-methoxy-2-propanol (PM2) and less than 5%, or less than 3%, or less than 1%, or even less than 0.3% 2-methoxy-1-propanol (PM1). As a result, the present process may advantageously be incorporated into a process for the production of an alkylene oxide and a stream of glycol ethers.

The provided processes will generally comprise reacting an alkylene with hydrogen peroxide, hydroperoxide, or hydrogen and oxygen under conditions sufficient to produce a product stream comprising the desired alkylene oxide. In some embodiments, the reaction will result in a product stream comprising from about from about 5 to about 15 weight percent alkylene oxide, about 50 to about 85 weight percent alkyl alcohol and about 10 to about 25 weight percent water, based upon the total weight of the mixture. Or, the product stream may comprise from about 6 to about 12 weight percent alkylene oxide, about 60 to about 80 weight percent alkyl alcohol and about 10 to about 20 weight percent water. In some embodiments, the product stream may even comprise from about 8 to about 10.5 weight percent alkylene oxide, about 65 to about 75 weight percent alkyl alcohol and about 10 to about 15 weight percent water.

Any alkylene may be reacted with the hydrogen peroxide, hydroperoxide, or oxygen and hydrogen, and the same may be selected based upon the alkylene oxide desirably produced. Suitable alkylenes include, for example, ethylene, propylene, butylene, pentylene, hexylene, and combinations thereof. In some embodiments, the alkylene oxide comprises propylene oxide.

The term "hydroperoxide" refers to a compound of the formula ROOH, wherein R is any substituted or unsubstituted $C_1$-$C_{15}$ alkyl, aryl or arylalkyl group. Examples of hydroperoxides suitable for use in the present processes include, but are not limited to, tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronapthhalene hydroperoxide, isobutylbenzene hydroperoxide, ethylnaphthalene hydroperoxide, and peracids such as peracetic acid. Mixtures of two or more hydroperoxides can also be used. In some embodiments, hydrogen peroxide is reacted with the desired alkylene. In such embodiments, the hydrogen peroxide is desirably provided as an aqueous hydrogen peroxide solution. Such a solution may comprise hydrogen peroxide in a concentration of from about 1 to about 90 wt %, or from about 10 to about 70 wt %, or from about 30 to about 50 wt %, based upon the total weight of the solution.

The reaction of the desired alkylene and hydrogen peroxide, hydroperoxide or oxygen and hydrogen may desirably be carried out in the presence of one or more catalysts. Suitable catalysts for epoxidation reactions include, but are not limited to, zeolites, and in particular, zeolites comprising titanium, e.g., titanium silicalites. In addition to titanium and silica, zeolite materials may comprise additional elements, such as, e.g., aluminum, zirconium, tin, iron, cobalt, nickel, gallium, boron, or fluorine. Zeolites comprising elements in place of titanium may also be used. For example, zeolites wherein the titanium is partially or completely replaced by vanadium, zirconium, niobium, or mixtures of these may be used.

In some embodiments, the zeolite catalyst comprises at least one of titanium, germanium, tellurium, vanadium, chromium, niobium, zirconium or combinations of these. In some embodiments, zeolite catalysts having a pentasil zeolite structure. When the zeolite catalyst comprises titanium such structures may include those assigned to structure types ITQ-4, ITQ-9, SSZ-24, TTM-1, UTD-1, CIT-1, CIT-5, ZSM-48, ZSM-12, MFI, MEL, MWW, BEA, TS-1, TS-2, TS3 or mixed structures of any of these, may be used, as can zeolites displaying a structure that is amorphous to zeolite beta.

The product stream produced by the reaction of the desired alkylene with the hydrogen peroxide, hydroperoxide, or hydrogen and oxygen in the presence of a catalyst, if desired, is then introduced into a distillation column to produce a refined stream. Desirably, the refined product stream will comprise from about 50 to about 99 weight percent alkylene oxide, about 0.5 to about 50 weight percent alkyl alcohol and about 0 to about 5 weight percent water. In some embodiments, e.g., wherein the alkyl alcohol comprises methanol and the alkylene oxide comprise propylene oxide, the refined stream may comprise 65 to about 99 weight percent alkylene oxide, about 0.5 to about 35 weight percent alkyl alcohol and about 0 to about 5 weight percent water. In such embodiments, the refined stream may comprise from about 70 weight percent to about 95 wt % alkylene oxide, from about 1 weight percent to about 30 wt % alkyl alcohol and from about 0.1 weight percent to about 4.9 wt % water. Or, the refined stream may comprise from about 70 weight percent to about 90 wt % alkylene oxide, from about 10 weight percent to about 30 wt % alkyl alcohol and from about 1 weight percent to about 4 wt % water.

Generally speaking, the distillation column utilized to provide the refined stream may comprise fewer than 80 theoretical stages, and may comprise, e.g., from about 15 to about 70 theoretical stages, or from about 30 to about 60 theoretical stages. The distillation column utilized to provide the refined stream will further desirably have a bottoms temperature of from about 40° C. to about 70° C., or from about 46° C. to about 64° C., or from about 52° C. to about 62° C. The distillation may be carried out at pressures of from about 300 mbar to about 1000 mbar, or from about 400 mbar to about 800 mbar, or from about 500 mbar to about 700 mbar, as measured at the top of the column.

The refined product stream is then reacted with a catalyst comprising a metal-ligand complex, an acid, a base, or a combination of any number of these. Such catalysts are described above. The resulting reacted stream comprises less than 1 wt % alkyl alcohol, from about 0.01 to about 98 weight percent alkylene oxide and from about 2 to about 99 weight percent glycol ethers.

The particular glycol ethers obtainable will depend upon the particular composition of the starting mixture, i.e., the particular alkyl alcohol and alkylene oxide in the mixture, as well as the particular catalyst chosen. For exemplary mixtures comprising, e.g., methanol and propylene oxide, the stream of glycol ethers may typically comprise greater than 50%, or greater than 80% or even greater than 95% of monopropylene glycol methyl ethers (PM), and less than 50%, or even less than 25% or even less than 5% dipropylene glycol monomethyl ether (DPM). The PM homologue typically further comprises greater than 95%, or greater than 97%, or even greater than 99% or even greater than 99.7% 1-methoxy-2-propanol (PM2) and less than 5%, or less than 3%, or less than 1%, or even less than 0.3% 2-methoxy-1-propanol (PM1).

In some embodiments, the reacted stream is then introduced into a second distillation column to provide a substantially pure stream of alkylene oxide and a stream of glycol ethers. In the exemplary embodiment, this second distillation column may advantageously be relatively simple, and well within the scope of knowledge of those of ordinary skill in the art. Because the use of the present process is expected to be useful in process for the production of alkylene oxide to reduce, or replace, any amount of extraction solvent that may otherwise be added, and further, a provide a stream of glycol ethers, the amount of which capable of being adjusted based upon the amount of alkyl alcohol allowed to remain in the partially refined alkylene oxide product stream the manufacturing equipment necessary to carry out the same is expected to be simplified as compared to the manufacturing equipment utilized to carry out the aforementioned processes. Furthermore, the process produces a substantially pure stream of alkylene oxide and a substantially pure stream of glycol ethers. And so, in another aspect, a hybrid manufacturing assembly for the production of an alkylene oxide and a stream of glycol ethers is provided.

Such an assembly is shown in FIG. 1. More particularly, the assembly 100 of FIG. 1 comprises a reactor 102, first distillation column 104, vessel 106 and second distillation column 108. More particularly, reactor 102 may comprise any reactor suitable to house the reaction to produce an alkylene oxide, e.g., as from the reaction of an alkylene with hydrogen peroxide in an alkyl alcohol solvent. For example, reactor 102 may be a fixed bed, a fluidized bed, or a continuous stirred tank reactor (CSTR), or a batch, semi-batch, or continuous reactor, or combinations thereof. Reactor 102 may be configured to operate isothermally, adiabatically, or a combination thereof. In some embodiments, reactor 102 comprises a supported catalyst.

Reactor 102 is operatively disposed relative to first distillation column 104 so that the product stream produced therein may be received by distillation column 104. Distillation column 104 is further configured to receive a product stream comprising from about 5 to about 15 weight percent alkylene oxide, about 50 to about 85 weight percent alkyl alcohol and about 10 to about 25 weight percent water, based upon the total weight of the product stream, and to produce a refined stream therefrom comprising from about 50 to about 99 weight percent alkylene oxide, about 0.5 to about 50 weight percent alkyl alcohol and about 0 to about 5 weight percent water. In some embodiments, e.g., wherein the alkyl alcohol comprises methanol and the alkylene oxide comprise propylene oxide, the refined stream may comprise 65 to about 99 weight percent alkylene oxide, about 0.5 to about 35 weight percent alkyl alcohol and about 0 to about 5 weight percent water.

Advantageously, first distillation column 104 may comprise fewer than 80 theoretical stages, and may comprise, e.g., from about 15 to about 70 theoretical stages, or from about 30 to about 60 theoretical stages. As is the case with reactor 102, the particular conditions at which first distillation column 104 is desirably operated will depend upon the composition of the product stream received thereby. In order to receive the product stream and provide the refined stream defined above, and in that exemplary embodiment wherein the alkyl alcohol comprises methanol and the alkylene oxide comprises propylene oxide, first distillation column 104 will desirably be operated at a bottoms temperature of from about 40° C. to about 70° C., or from about 46° C. to about 64° C., or from about 52° C. to about 62° C. The distillation may be carried out at pressures of from about 300 mbar to about 1000 mbar, or from about 400 mbar to about 800 mbar, or from about 500 mbar to about 700 mbar, as measured at the top of the column.

First distillation column 104 is operatively disposed to vessel 106, so that vessel 106 may receive a refined stream therefrom. Vessel 106 may comprise any vessel or reactor suitable to house the alkanolysis reaction, and if desired, the chosen catalyst. As such, vessel 106 may be a fixed bed, a fluidized bed, or a continuous stirred tank reactor (CSTR), or a batch, semi-batch, or continuous reactor, or combinations of these. Vessel 106 may be configured to operate isothermally, adiabatically, or a combination thereof. In some embodiments, vessel 106 comprises a fixed bed reactor, comprising a supported metal ligand complex catalyst that is typically operated isothermally.

The particular conditions at which vessel 106 is operated will depend upon the particular alkyl alcohol desirably removed from the refined stream received from distillation column 104 by vessel 106 and the catalyst chosen to do so. For the exemplary embodiment wherein the alkyl alcohol comprises methanol and the catalyst comprises a metal-ligand complex according to Formula I, above, vessel 106 may typically be operated at temperatures of from about −10° C. to about 130° C., or from about 10° C. to about 100° C. or from about 20° C. to about 60° C., and pressures of from about 14.5 psig to about 300 psig, or from about 14.5 psig to about 150, or from about 14.5 psig to about 75 psig.

A second distillation column 108 is operatively disposed relative to vessel 106 to receive a reacted stream therefrom. Second distillation column is desirably configured to receive a reacted stream comprising less than 1 wt % alkyl alcohol, from about 0.01 wt % to about 98 wt % alkylene oxide, and from about 2 wt % to about 99 wt % glycol ethers, or less than about 0.8 wt % alkyl alcohol and from about 10 wt % to about 90 wt % alkylene oxide, and from about 10 wt % to about 90 wt % glycol ethers, or less than about 0.7 wt % alkyl alcohol and from about 50 wt % to about 85 wt % alkylene oxide, and from about 15 wt % to about 50 wt % glycol ethers, and to produce a substantially pure stream of alkylene oxide and a stream of glycol ethers therefrom.

The following examples are set forth for the purpose of illustrating the invention; but these examples are not intended to limit the invention in any manner. One skilled in the art will recognize a variety of substitutions and modifications of the examples that will fall within the scope of the invention.

Example 1. Comparative Propylene Oxide Purification Process

Propylene is converted to propylene oxide by reacting propylene with hydrogen peroxide in the presence of methanol as a solvent and TS-1 catalyst (in a two stage reaction process with separation steps to remove the raw materials from the crude propylene oxide product stream.

After separation of the unreacted propylene from the effluent stream, the crude oxide stream (9.49 wt % propylene oxide, 72.38 wt % methanol, 17.60 wt % water, 0.43 wt % propylene glycol methyl ether, 0.05 wt % propylene glycol, 0.01 wt % propylene, 0.03 wt % acetaldehyde, and 0.01 wt % formaldehyde) is separated in a distillation stage at 0.5 bar with 80 theoretical stages to obtain a top mixture comprising of propylene oxide with less than 0.001 wt % methanol, and a bottoms mixture with less than 0.005 wt % propylene oxide. With a crude oxide feed stream of 740,000 lb/hr to the tenth stage from the top of the distillation tower (typically referred to as the condenser), the separation of the purified propylene oxide product can be achieved with a reflux ratio of 6.73 at the top of the tower and 0.34 boilup ratio at the bottom of the tower (typically referred to as the reboiler). The resulting heat duty of the separation is −33.82 Megawatt (MW) in the condenser and 41.41 MW in the reboiler.

Example 2

Propylene is converted to propylene oxide by reacting propylene with hydrogen peroxide in the presence of methanol as a solvent and TS-1 catalyst in a two stage reaction process (e.g., conducted within reactor 102) with separation steps to remove the raw materials from the crude propylene oxide product stream.

After separation of the unreacted propylene from the effluent stream of reactor 102, the crude oxide stream (9.49 wt % propylene oxide, 72.38 wt % methanol, 17.60 wt % water, 0.43 wt % propylene glycol methyl ether, 0.05 wt % propylene glycol, 0.01 wt % propylene, 0.03 wt % acetaldehyde, and 0.01 wt % formaldehyde) is separated in distillation column 104 at 0.5 bar with 80 theoretical stages to obtain a top mixture comprising of propylene oxide with 10.0 wt % methanol, and a bottoms mixture with less than 0.005 wt % propylene oxide. With a crude oxide feed stream of 740,000 lb/hr to the tenth stage from the top of distillation column 104, the separation can be achieved with a reflux ratio of 3.37 at the top of distillation column 104 and 0.262 boilup ratio at the bottom of distillation column 104. The resulting heat duty of the separation is −24.48 MW in the condenser and 32.05 MW in the reboiler.

The top mixture from distillation column 104 (74,448 lb/hr) comprising of 89.5 wt % propylene oxide and 10.0 wt % methanol is pumped to reactor vessel 106 containing the metal-ligand complex catalyst. In reactor vessel 106, the methanol reacts with the propylene oxide to form a 330:1 monopropylene glycol methyl ether mixture of 1-methoxy-2-propanol (PM-2) and 2-methoxy-1-propanol (PM-1). In the isothermal reactor vessel 106, 99.95% of the methanol in the reactor feed stream is converted to propylene glycol ethers. The exothermic reaction between the methanol and propylene oxide in the reactor vessel 106 requires cooling duty of −1.81 MW to maintain the reaction temperature of 60° C.

The reactor effluent stream from reactor vessel 106, consisting of 71.4 wt % propylene oxide, 28.03 wt %1-methoxy-2-propanol (PM-2) and 0.08 wt % 2-methoxy-1-propanol (PM-1), is separated in distillation column 108 at 0.5 bar with 25 theoretical stages to obtain a top mixture comprising of propylene oxide with less than 0.001 wt % alcohols comprising of methanol and propylene glycol methyl ethers, and a bottoms mixture comprising monopropylene glycol methyl ether with less than 0.005 wt % propylene oxide. With a feed stream of 78,448 lb/hr to the distillation column 108, the separation can be achieved with a reflux ratio of 0.15 at the top of distillation column 108 and 2.811 boilup ratio at the bottom of distillation column 108. The resulting heat duty of the separation is −4.03 MW in the condenser and 3.58 MW in the reboiler.

As shown in Table 1, the total heat duty of the conventional process (75.27 MW) described in Comparative Example 1 is greater than the 66.65 MW required for the inventive process, even using an 80 stage distillation column 104 (Example 2). Table 1 also shows that the most energy intensive portion of the refining process is the first separation step (at distillation column 104) where the propylene oxide is concentrated from the mostly methanol feed material. The results in Table 1 show that the majority of the energy savings are achieved by lowering the propylene oxide purity in distillation column 104; 75.27 MW are required for 0.001% methanol (Example 1) compared to 56.53 MW for 10 wt % methanol (Example 2).

Example 3

Propylene is converted to propylene oxide by reacting propylene with hydrogen peroxide in the presence of methanol as a solvent and TS-1 catalyst within reactor 102 in a two stage reaction process with separation steps to remove the raw materials from the crude propylene oxide product stream.

After separation of the unreacted propylene in the effluent stream from reactor 102, the crude oxide stream (9.49 wt % propylene oxide, 72.38 wt % methanol, 17.60 wt % water, 0.43 wt % propylene glycol methyl ether, 0.05 wt % propylene glycol, 0.01 wt % propylene, 0.03 wt % acetaldehyde, and 0.01 wt % formaldehyde) is separated within distillation column 104 at 0.5 bar with 40 theoretical stages to obtain a top mixture comprising of propylene oxide with 10.0 wt % methanol, and a bottoms mixture with less than 0.005 wt % propylene oxide. With a crude oxide feed stream of 740,000 lb/hr to the sixth stage from the top of distillation column 104, the separation can be achieved with a reflux ratio of 3.89 at the top of distillation column 104 and 0.286 boilup ratio at the bottom of distillation column 104. The resulting heat duty of the separation is −27.43 MW in the condenser and 35.00 MW in the reboiler.

The top mixture from distillation column 104 (74,448 lb/hr) comprising of 89.5 wt % propylene oxide and 10.0 wt % methanol is pumped to reactor vessel 106 containing the metal-ligand complex catalyst. In reactor vessel 106, the methanol reacts with the propylene oxide to form a 330:1 monopropylene glycol methyl ether mixture of 1-methoxy-2-propanol (PM-2) and 2-methoxy-1-propanol (PM-1). In the isothermal reactor, 99.95% of the methanol in the reactor feed stream is converted to propylene glycol ethers. The exothermic reaction between the methanol and propylene oxide in reactor vessel 106 requires cooling duty of −1.81 MW to maintain the reaction temperature of 60° C.

The reactor effluent stream from reactor vessel 106, consisting of 71.4 wt % propylene oxide, 28.03 wt %1-methoxy-2-propanol (PM-2) and 0.08 wt % 2-methoxy-1-propanol (PM-1) is separated within distillation column 108 at 0.5 bar with 25 theoretical stages to obtain a top mixture comprising of propylene oxide with less than 0.001 wt % alcohols comprising of methanol and propylene glycol methyl ethers, and a bottoms mixture comprising monopropylene glycol methyl ether with less than 0.005 wt % propylene oxide. With a feed stream of 78,448 lb/hr to the distillation column 108, the separation can be achieved with a reflux ratio of 0.15 at the top of distillation column 108 and 2.811 boilup ratio at the bottom of distillation column 108. The resulting heat duty of the separation is −4.03 MW in the condenser and 3.58 MW in the reboiler.

As shown in Table 1, the total heat duty of the hybrid process with the smaller distillation column (Example 3) is less than the conventional process (Example 1), but greater than the hybrid process with the 80 stage column (Example 2). The lower number of theoretical trays for distillation column 104 in Example 3 to achieve the desired separation would significantly lower the relative capital cost for the process.

Example 4

Propylene is converted to propylene oxide by reacting propylene with hydrogen peroxide in the presence of methanol as a solvent and TS-1 catalyst within reactor 102 in a two stage reaction process with separation steps to remove the raw materials from the crude propylene oxide product stream.

After separation of the unreacted propylene in the effluent stream from reactor 102, the crude oxide stream (9.49 wt % propylene oxide, 72.38 wt % methanol, 17.60 wt % water, 0.43 wt % propylene glycol methyl ether, 0.05 wt % propylene glycol, 0.01 wt % propylene, 0.03 wt % acetaldehyde, and 0.01 wt % formaldehyde) is separated within distillation column 104 at 0.5 bar with 40 theoretical stages to obtain a top mixture comprising of propylene oxide with 20.0 wt % methanol, and a bottoms mixture with less than 0.005 wt % propylene oxide. With a crude oxide feed stream of 740,000 lb/hr to the sixth stage from the top of distillation column 104, the separation can be achieved with a reflux ratio of 2.75 at the top of distillation column 104 and 0.282 boilup ratio at the bottom of distillation column 104. The resulting heat duty of the separation is −26.47 MW in the condenser and 34.03 MW in the reboiler.

The top mixture from distillation column 104 (88,300 lb/hr) comprising of 79.5 wt % propylene oxide and 20.0 wt % is pumped to reactor vessel 106 containing the metal-ligand complex catalyst. In reactor vessel 106, the methanol reacts with the propylene oxide to form a 330:1 monopropylene glycol methyl ether mixture of 1-methoxy-2-propanol (PM-2) and 2-methoxy-1-propanol (PM-1). In the isothermal reactor vessel 106, 99.95% of the methanol in the reactor feed stream is converted to propylene glycol ethers. The exothermic reaction between the methanol and propylene oxide in reactor vessel 106 requires cooling duty of −5.16 MW to maintain the reaction temperature of 60° C.

The reactor effluent stream from reactor vessel 106, consisting of 43.3 wt % propylene oxide, 56.1 wt %1-methoxy-2-propanol (PM-2) and 0.16 wt % 2-methoxy-1-propanol (PM-1) is separated within distillation column 108 at 0.5 bar with 25 theoretical stages to obtain a top mixture comprising of propylene oxide with less than 0.001 wt % alcohols comprising of methanol and propylene glycol methyl ethers, and a bottoms mixture comprising monopropylene glycol methyl ether with less than 0.005 wt % propylene oxide. With a feed stream of 88,300 lb/hr to distillation column 108, the separation can be achieved with a reflux ratio of 0.318 at the top of distillation column 108 and 0.920 boilup ratio at the bottom of distillation column 108. The resulting heat duty of the separation is −3.16 MW in the condenser and 3.26 MW in the reboiler.

As shown in Table 1, the total heat duty of the hybrid process with the smaller distillation column with higher methanol concentration (Example 4) is less than the conventional process (Example 1). The total heat duty for the process with 20% methanol in the top stream from distillation column 104 (Example 4) is slightly higher than with 10% methanol (Example 3). The total heat duty for the distillation column 104 with 20% methanol in the top stream (Example 4) is slightly lower than with the same system with 10% methanol (Example 3). However, the higher amount of methanol in the top stream from distillation column 104 results in a higher heat duty for the reactor vessel 106 and distillation column 108.

TABLE 1

|  | Example 1 | Example 2 | Example 3 | Example 4 |
|---|---|---|---|---|
| Column 104 Stages | 80 | 80 | 40 | 40 |
| Column 104 Condenser Duty (MW) | −33.82 | −24.48 | −27.43 | −26.47 |
| Column 104 Reboiler Duty (MW) | 41.41 | 32.05 | 35 | 34.03 |
| Reactor 106 Cooling Duty (MW) |  | −1.81 | −1.81 | −5.16 |
| Column 108 Condenser Duty (MW) |  | −4.03 | −4.03 | −3.16 |
| Column 108 Reboiler Duty (MW) |  | 3.58 | 3.58 | 3.26 |
| Total Cooling Duty (MW) | −33.82 | −30.32 | −33.27 | −34.79 |
| Total Heating Duty (MW) | 41.41 | 35.63 | 38.58 | 37.29 |
| Total Heat Transfer Duty (MW) | 75.27 | 65.95 | 71.85 | 72.08 |

The total production rate of purified propylene oxide material is lower with the hybrid process due to the conversion of methanol and propylene oxide to propylene glycol methyl ether in reactor vessel 106 between the two distillation columns (104 and 108) in the hybrid process. As shown in Table 2, the propylene oxide production is 20% lower than the conventional process with 10% methanol in the top stream from the distillation column 104 (Examples 2 and 3) and 45% lower with 20% methanol (Example 4). Due to the conversion of propylene oxide to propylene glycol methyl ether in the hybrid process, the total heat duty per unit of propylene oxide is higher with hybrid process. However, the total heat duty per unit of final product (propylene oxide and propylene glycol ether) is significantly lower with the hybrid process compared to the conventional process (Example 1).

TABLE 2

|  | Example 1 | Example 2 | Example 3 | Example 4 |
|---|---|---|---|---|
| Propylene Oxide (mT/hr) | 32.01 | 25.57 | 25.57 | 17.50 |
| Propylene Glycol Methyl Ether (mT/hr) |  | 10.00 | 10.00 | 22.55 |
| Total Final Products (mT/hr) | 32.01 | 35.57 | 35.57 | 40.05 |
| Total Heat Duty (MW) | 75.27 | 65.95 | 71.85 | 72.08 |
| Total Heat Duty per metric ton of PO (MW/mT) | 2.35 | 2.58 | 2.81 | 4.12 |
| Total Heat Duty per metric ton of product (MW/mT) |  | 1.85 | 2.02 | 1.80 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A manufacturing assembly for the production of an alkylene oxide and one or more glycol ethers, the assembly comprising: a reactor appropriate for housing a reaction to produce an alkylene oxide product stream; an exit stream of the reactor being the alkylene oxide product stream com- prising from about 5 to about 15 weight percent alkylene oxide, about 50 to about 85 weight percent alkyl alcohol, and about 10 to about 25 weight percent water; a first distillation column that is operatively disposed relative to the reactor and that receives the alkylene oxide product stream from the reactor, the first distillation column comprising fewer than 80 theoretical stages; an exit stream of the first distillation column being a refined stream comprising from about 70 to about 95 weight percent alkylene oxide, about 1 to about 30 weight percent alkyl alcohol, and about 0.1 to about 4.9 weight percent water; a vessel operatively that is disposed relative to the first distillation column and that receives the refined stream from the first distillation column and housing a catalyst capable of reacting with the refined stream; an exit stream of the vessel being a reacted stream comprising reacted stream comprising less than 1 wt % alkyl alcohol, from about 0.01 to about 98 weight percent alkylene oxide, and from about 2 to about 99 weight percent glycol ethers; and a second distillation column that is operatively disposed relative to the vessel and that receives the reacted stream from the vessel; and an exist stream of the second distillation being a stream of alkylene oxide and a stream of glycol ethers.

2. The manufacturing assembly of claim 1, wherein the alkylene oxide comprises ethylene oxide, propylene oxide, butylene oxide, pentylene oxide, hexylene oxide, and combinations thereof.

3. The manufacturing assembly of claim 1, wherein said alkylene oxide is propylene oxide.

4. The manufacturing assembly of claim 1, wherein the alcohol comprises methanol, ethanol, propanol, butanol, pentanol, hexanol, 2-ethylhexyl alcohol, and combinations thereof.

5. The manufacturing assembly of claim 1, wherein the alcohol comprises methanol.

6. The manufacturing assembly of claim 1, wherein the catalyst comprises a metal-ligand complex, an acid, a base, or a combination of any number of these to produce a reacted stream comprising less than 1 wt % alkyl alcohol from about 0.01 to about 98 weight percent alkylene oxide and from about 2 to about 99 weight percent glycol ethers; wherein the metal ligand complex comprises a monomer defined by the formula:

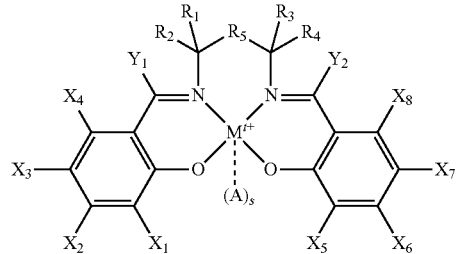

wherein $R_1$, $R_2$, $R_3$, $R_4$, $Y_1$, $Y_2$, $X_1$, $X_2$, $X_3$, $X_4$, $X_5$, $X_6$, $X_7$, and $X_8$ comprise, independently of one other, substituents selected from the group consisting of hydrogen, halogen, alkyl, alkenyl, alkynyl, hydrocarbyl, hydroxyl, alkoxyl, amino, nitro, amide, phosphoryl, phosphonate, phosphine, carbonyl, carboxyl, silyl, ether, thioether, sulfonyl, selenoether, ketone, aldehyde, and ester;

or wherein two or more of $R_1$, $R_2$, $R_3$, $R_4$, $Y_1$, $Y_2$, $X_1$, $X_2$, $X_3$, $X_4$, $X_5$, $X_6$, $X_7$, and $X_8$ together form a ring selected from the group consisting of a carbocyclic ring and a heterocyclic ring, said ring having from 4 to 10 atoms in the ring;

wherein $R_5$ group is selected from the group comprising a carbon-carbon bond, a methylene group, an ethylene group, an amine, an oxygen atom, and a sulfur atom;

wherein $M^{t+}$ is a Group 2-15 metal capable of complexing with a ligand to affect catalysis, wherein t is an integer between 2 and 4;

wherein group A is selected from the group consisting of neutral group, bound anionic group, unbound anionic group, and combinations thereof, wherein s is the number of A groups associated with the metal and is an integer between 0 and 2.

* * * * *